United States Patent [19]

Harmony et al.

[11] Patent Number: 4,909,949

[45] Date of Patent: * Mar. 20, 1990

[54] BRIDGE FOR SUSPENDING A BLOOD COLLECTION BAG

[75] Inventors: Daniel C. Harmony, Tucson, Ariz.; Bradley T. Noble, Greeley, Colo.

[73] Assignee: Engineering & Research Associates, Ariz.

[*] Notice: The portion of the term of this patent subsequent to Jun. 28, 2006 has been disclaimed.

[21] Appl. No.: 113,626

[22] Filed: Oct. 26, 1987

[51] Int. Cl.⁴ .................... B01D 21/26; B04B 15/00
[52] U.S. Cl. .................... 210/787; 210/513; 494/20; 494/21; 494/37; 494/45
[58] Field of Search .................... 494/16, 20, 21, 45, 494/37; 222/95, 103; 210/782, 787, 789, 360.1, 361, 512.1, 513, 514

[56] References Cited

U.S. PATENT DOCUMENTS

| | | | |
|---|---|---|---|
| 4,439,177 | 3/1984 | Conway | 494/20 |
| 4,543,084 | 9/1985 | Bailey | 494/20 |
| 4,753,739 | 6/1988 | Noble | 210/787 |

Primary Examiner—W. Gary Jones
Attorney, Agent, or Firm—Cahill, Sutton & Thomas

[57] ABSTRACT

A bridge is attachable to and mountable upon the upper edge of a centrifuge cup for suspending a blood collection bag within the cavity of the centrifuge cup during centrifugation of the collected blood. The bridge includes structure for supporting the bridge upon an expressor to permit expressing the centrifuged blood from the bridge suspended blood collection bag.

42 Claims, 3 Drawing Sheets

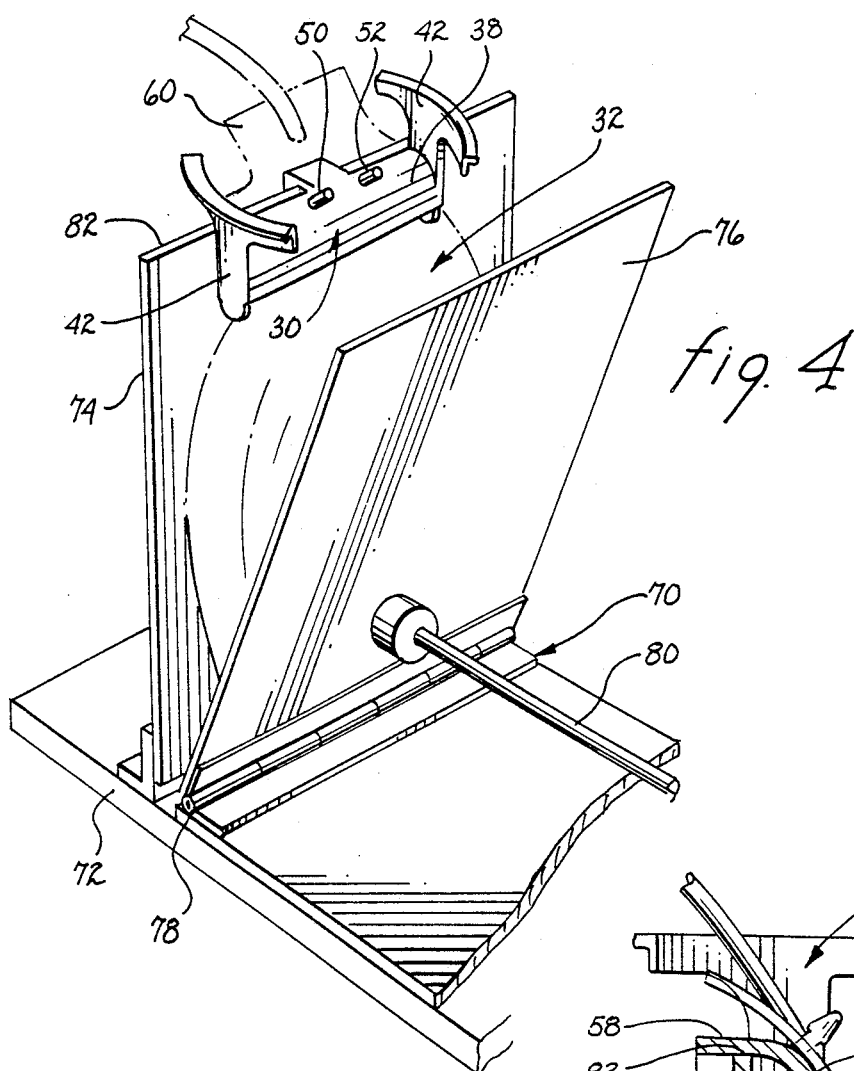
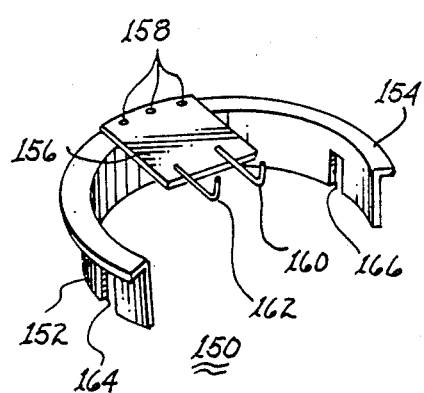
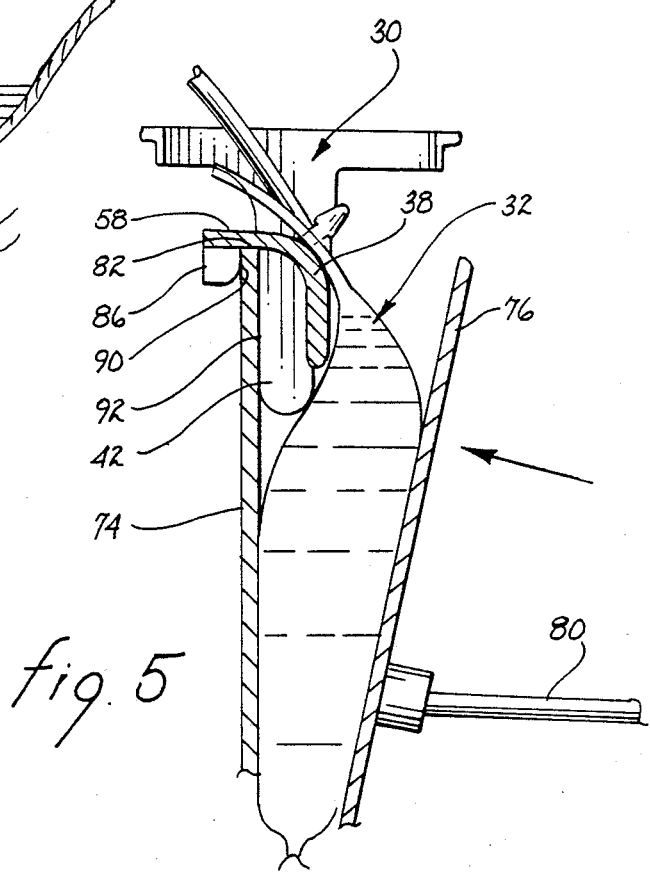

BRIDGE FOR SUSPENDING A BLOOD COLLECTION BAG

CROSS REFERENCE TO RELATED APPLICATIONS

The present invention is related to an invention described in a copending application for United States Patent entitled "BLOOD BAG SUPPORT SYSTEM", Ser. No. 822,381, and filed on Jan. 27, 1987, now U.S. Pat. No. 4,753,739, which application is assigned to the present Assignee.

BACKGROUND OF THE INVENTION

1. Field of the Invention

The present invention relates to blood collection bag support systems and, more particularly, to apparatus for suspending a blood collection bag within a centrifuge cup and in an expressor.

2. Description of Prior Art

Blood collection bags of a certain size, shape and configuration have been employed by blood collection centers, hospitals and other medical facilities for decades to collect and store blood and components thereof. Typically, whole blood within a blood collection bag is centrifuged to separate the plazma, platelets, red blood cells and white blood cells. Industry standard centrifuges for this purpose include a plurality of cups for receiving and containing the blood collection bags during the centrifugation process.

During centrifugation of the blood collection bags, it is important that the blood collection bag and components associated therewith not be creased, folded or otherwise be configured to permit retention of a quantity of blood apart from the main body of blood. If such retention occurs, contamination of the separated blood components subsequent to centrifugation by mixing with the segregated quantity of blood could occur. It is therefore important to mount the blood collection bag within the centrifuge cup in such a manner that physical segregation of a quantity of blood not occur. In the above identified related United States Patent, there is described a pair of supports locatable within a centrifuge cup for suspendingly supporting a blood collection bag therebetween. The point of suspension is from preformed apertures located at the upper end of the conventional blood collection bag and peripheral to the envelope portion containing the blood to be centrifuged. Such suspension discourages creasing or folding of the blood collection bag and segregated retention of a quantity of whole blood is prevented.

SUMMARY OF THE INVENTION

The present invention is directed to a bridge extending generally diametrically across the cavity of a centrifuge cup to facilitate insertion and removal of the suspended blood collection bag. After centrifugation, the blood components may be expressed from the blood collection bag by any one of several conventional expressors. The bridge, with the blood collection bag suspended therefrom, includes structure for receiving a part of the expressor to locate and lodge the bridge thereupon while maintaining the blood collection bag suspended therefrom in a configuration to be acted upon by the expressor. To simplify use and mounting/dismounting of the blood collection bag, the bridge may be of monolithic structure to circumvent the need for manipulating components of the bridge during attachment and detachment of the blood collection bag.

It is therefore a primary object of the present invention to provide a bridge for suspending a blood collection bag in a centrifuge cup.

Another object of the present invention is to provide a bridge extending across the cavity of a centrifuge cup for suspending within the cup a blood collection bag.

Yet another object of the present invention is to provide a monolithic bridge for suspending a blood collection bag in a centrifuge cup.

Still another object of the present invention is to provide a bridge mountable upon each of a centrifuge cup and an expressor to suspend a blood collection bag therefrom.

A further object of the present invention is to provide a bridge which is readily attachable to and detachable from a centrifuge cup for freely spending a blood collection bag within the centrifuge cup.

A yet further object of the present invention is to provide a method for suspending a blood collection bag within a centrifuge cup.

A still further object of the present invention is to provide a method for serially suspending a blood collection bag from each of a centrifuge cup and an expressor.

These and other objects of the present invention will become apparent to those skilled in the art as the description thereof proceeds.

BRIEF DESCRIPTION OF THE DRAWINGS

FIG. 4 illustrates the attachment of the bridge to an expressor;

FIG. 5 is a partial cross sectional view illustrating a blood collection bag within an expressor and suspended from the bridge;

FIG. 6 illustrates a variant of a bridge for suspending a blood collection bag;

FIG. 7 illustrates mounting of the variant shown in FIG. 6 upon an expressor;

FIG. 8 is a partial exploded view of a further variant of a bridge for supporting a blood collection bag;

FIG. 9 is a partial cross sectional view taken along lines 9—9, as shown in FIG. 8, and illustrating attachment of a further variant to an expressor; and FIG. 10 is a perspective view of a yet further variant of a bridge.

DESCRIPTION OF THE PREFERRED EMBODIMENT

Figure 1:
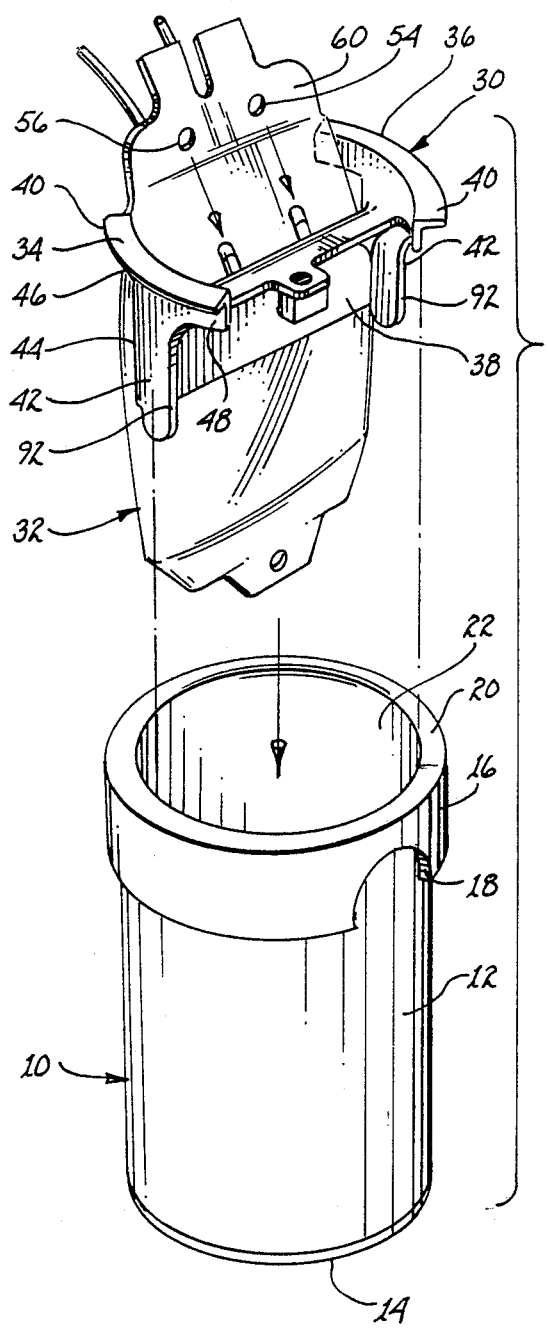
FIG. 1 illustrates the operative relationship between a bridge, a blood collection bag and a centrifuge cup.

Referring to FIG. 1, there is illustrated, in representative form, a conventional centrifuge cup 10. Such a cup may include a cylindrical body 12 having a closed bottom 14. It is to be understood that other configurations of the lower end portion of centrifuge cup 10 are known and have been used. Generally, a collar 16 is formed about the upper end of the centrifuge cup, which collar may include diametrically opposed insets 18. These insets are used to receive the respective ends of opposed studs of a yoke which permit pivotal movement of the centrifuge cup about the longitudinal axis of the studs in response to the forces imposed during centrifugation. The upper end of the centrifuge cup includes an annular edge 20 which may lie in a plane perpendicular to the longitudinal axis of the centrifuge cup. Generally, a cylindrical surface 22 is formed within the major part of body 12. The lower end of this cylindrical surface is necessarily in conformance with the configuration of the bottom of the centrifuge cup. A bridge 30 is associated with and supported by the upper end of centrifuge cup 10 to suspend a conventional blood collection bag 32.

Figure 2:
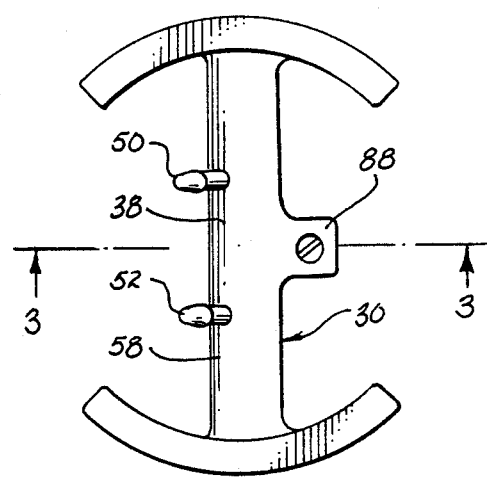
FIG. 2 is a top view of the bridge.
Figure 3:
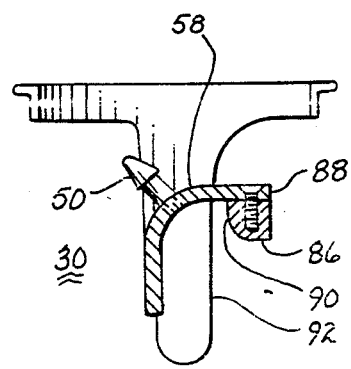
FIG. 3 is a cross sectional view taken along lines 3—3, as shown in FIG. 2.

The bridge will be described in further detail with joint reference to FIGS. 1, 2 and 3. The bridge includes a pair of opposed seating members 34, 36 joined by a cross member 38. Each seating member includes a segment of an annular flange 40 extending radially outwardly from a guide member 42. Each guide member may include a base 44 having a pair of arms 46, 48 extending laterally in opposed directions from the upper end of the base. The outside surface defined by the base and the pair of arms is curved in a cylindrical manner to conform with the curvature of cylindrical surface 22 of centrifuge cup 10. Flange 40 is configured to mate with and rest upon edge 20 of the centrifuge cup. By appropriate sizing of the length of cross member 38, seating members 34, 36 are maintained against the corresponding portions of cylindrical surface 22 such that flanges 40 firmly support bridge 30 at the upper end of centrifuge cup 10.

Bridge 30 includes a pair of pins 50, 52 extending therefrom for penetrably engaging correspondingly located apertures 54, 56 formed in the upper end of blood collection bag 32. Preferably, pins 50, 52 are oriented at an angle of 20° off vertical. By developing the cross member with a longitudinally extending curved surface 58 upper end 60 (see FIG. 1) of the blood collection bag and including the ports to the blood collection bag, will be tilted rearwardly from the main body of the bag, which orientation appears to be of assistance in urging downward flow of whole blood therefrom. By employing curved surface 58 adjacent upper end 60 of the blood collection bag, a further benefit is achieved. Because the blood collection bag is suspended from pins 50, 52, substantial loads are imposed upon apertures 54, 56 during centrifugation which may cause tearing at the apertures. By having upper end 60 laid back upon curved surface 58, the upper end will be urged thereagainst during centrifugation of the blood collection bag. Such urging will create a frictional contact therebetween, which friction will assist in providing support for the depending blood collection bag and the stresses imposed upon apertures 54, 56 will be lessened. Secondarily, by tilting the upper end of the blood collection bag laterally, the upper end, ports and tubing extending therefrom will be unlikely to protrude above the centrifuge cup. Such lack of protrusion is important in that the yoke from which the centrifuge cup is suspended usually has limited clearance at the upper end of the centrifuge cup during rotation of the centrifuge cup relative to the yoke in response to the centrifugal forces imposed.

Aside from supporting cross member 38, opposed bases 42 have a secondary function in assisting insertion and removal of the blood collection bag with respect to centrifuge cup 10. That is, they act in the manner of guides to orient and align the bridge with the cylindrical axis of cylindrical surface 22 upon insertion and removal of the bridge.

Referring jointly to FIGS. 4 and 5, there is illustrated in representative form an expressor 70. A conventional expressor, such as expressor 70, includes a base 72 for fixedly supporting a vertical plate 74. A plate 76 is pivotally attached to base 72 by pivot means 78. A manually or mechanically operated arm 80 urges pivotal movement of plate 76 toward and away from plate 74. Expressor 70 is used for the purpose of expressing form within a blood collection bag 32 the stratified layers of the blood components after centrifugation. To prevent remixing of the stratified layers, it is important to minimize jostling of the blood collection bag. As particularly illustrated in FIGS. 2 and 3, bridge 30 includes means for supporting the bridge and the depending blood collation bag upon plate 74. Such supporting means includes a stud 86 extending downwardly from a tab 88 of the cross member. Inner surface 90 of the stud, in combination with edges 92 of bases 42 define a three point supporting means for engaging upper edge 82 of plate 74, as particularly illustrated in FIG. 5.

In operation, bridge 30 may be manually lifted out of centrifuge cup 10 with blood collection bag 32 depending therefrom after centrifugation of the blood collection bag. By carefully lowering the bag adjacent plate 74 of expressor 70, the upper edge 82 of the plate can be easily nested within the three point supporting means of bridge 30 with minimal effort. Thus, jostling or jiggling of the blood collection bag during removal from the centrifuge cup, transport to the expressor and mounting upon the expressor can be essentially eliminated by an operator of even modest skill.

After attachment of bridge 30 to the expressor, plate 76 can be pivotally moved, as representatively illustrated in FIG. 5, by translation of handle 80 to express from within blood collection bag 32 the stratified contents. After the components of interest have been expressed, the blood collection bag is readily disengaged from the bridge by simply manually pulling upon upper end 60 to disengage apertures 54, 56 from supporting pins 50, 52. Thereafter, the bridge may be cleaned, if necessary, and reused. It may also be noted that the bridge can be manufactured as a monolithic unit of either metal or plastic by conventional manufacturing techniques.

Referring to FIG. 6, there is illustrated a first variant 100 of bridge 30. The variant includes a cross member 102 disposed intermediate guide members 104. The cross member may be essentially flush or aligned with the upper edge of the guide members as illustrated; alternatively, the cross member may be recessed downwardly from the upper edge of the guide members, as illustrated in FIGS. 1 and 3. Each of guide members 104 may include a slot 106, which slots are aligned with one another. A pair of pins 108, 110 extend from cross member 102 to penetrably engage commensurate apertures within upper end 60 of blood collection bag 32 whereby the blood collection bag depends from the cross member.

When variant 100 is used with a conventional expressor (of the type illustrated in FIG. 4), upper edge 82 of plate 74 is penetrably inserted into slots 106 of guide members 104. These slots are of sufficient depth to provide a solid point of support for the bridge with respect to the expressor. After the blood bag has been mounted upon expressor 70, the stratified components within a blood collection bag may be expressed in the conventional manner.

FIGS. 8 and 9 illustrate a second variant 120 of bridge 30. The variant includes guide members 122, 124 for supporting variant 120 in centrifuge cup 10, in the manner illustrated in FIG. 1. Each of the guide members includes a cylindrical surface 126, 128 which conforms with the cylindrical surface 22 of the centrifuge cup. An annular flange 130 supports guide member 122 upon edge 20 of the centrifuge cup and annular flange 132 supports guide member 124 upon the edge.

Guide member 122 includes a pair of rods 134, 136 extending inwardly therefrom in spaced apart relationship commensurate with the spacing between apertures 54, 56 in upper end 60 of blood collection bag 32 for penetrable engagement therewith. A pair of at least partially hollow rods 138, 140 extend inwardly from guide member 124 for telescoping engagement with rods 134 and 136, respectively. Accordingly, blood collection bag 32 is suspended from rod pairs 134, 138 and 136, 140 intermediate guide members 122, 124. Cylindrical keepers 142 mounted upon the rods are slidably engagable therewith to maintain the penetrably engaged part of upper end 60 of the blood collection bag in fixed spatial relationship between guide members 122, 124.

Guide member 122 includes a slot 150, as illustrated in FIGS. 8 and 9, extending chordwise through the guide member. The width of the slot is sufficient to snugly engage edge 82 and the upper end of plate 74 of a conventional expressor 70, as shown in FIG. 9. Furthermore, slot 150 is of sufficient depth to firmly support variant 120 and blood collection bag 32 suspended therefrom. In this manner, variant 120 may be lifted from centrifuge cup 10 after the blood collection bag has been centrifuged and mounted upon expressor 70 with a minimum jostling or jiggling of the blood collection bag. After the stratified components of interest have been expressed from blood collection bag 32, the blood collection bag may be disengaged from variant 120. Such disengagement is readily effected by pulling guide members 122, 124 apart to disengage the telescopingly mated rods. Thereafter, the collection bag can be pulled off the pair of rods still penetrably engaging the apertures in the upper end of the bag. Variant 120 is now ready for reuse.

In FIG. 10 there is shown a yet further variant 150 of bridge 30. A partially circular shroud 152, which may be segmented, depends from a segment of an annular flange 154. The shroud conforms in curvature with cylindrical surface 22 of centrifuge cup 10 (see FIG. 1) to establish a tight, but sliding, fit therebetween. The annular flange rests upon edge 20 of the centrifuge cup to support variant 150. A bracket 156 is attached to flange 154 by rivets 158, or the like. The bracket extends radially inwardly from the flange to support a blood collection bag from pins or hooks 106, 162. The hooks may be formed as part of the bracket or they may be attached thereto. The hooks are dimensioned and spaced apart from one another commensurate with apertures 54, 56 at the upper end 60 of a blood collection bag 32. A air of slots 164, 166 are formed in shroud 152 for receiving edge 82 and the upper end of plate 74 of an expressor 70 (see FIG. 4 and 5).

In operation, variant 150 is inserted with a centrifuge cup to support a blood collection bag suspended from hooks 106, 162 by sealing flange 154 upon edge 20. After centrifugation, the variant is lifted out of the centrifuge cup with the blood collection bag depending therefrom and mounted upon expressor 70 by inserting the upper end of plate 74 into slots 164 and 166. The stratified contents of the blood collection bag can then be expressed.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirement without departing from those principles.

We claim:

1. A bridge for suspending a blood collection bag within a centrifuge cup having an edge circular in planform at its open upper end and a longitudinal axis, said bridge comprising in combination:
   (a) a pair of guide members for engaging and receiving support from the upper end of the centrifuge cup, each guide member of said pair of guide members including means for seating said pair of guide members upon the edge of the centrifuge cup;
   (b) a cross member extending between said guide members; and
   (c) means for suspending the blood collection bag from said cross member.

2. The bridge as set forth in claim 1 wherein said seating means defines an arc commensurate with a segment of the edge of the centrifuge cup.

3. The bridge as set forth in claim 1 wherein said suspending means includes a pair of pins.

4. The bridge as set forth in claim 3 wherein said pair of pins are oriented at an angle of 20° off the longitudinal axis of the centrifuge cup upon seating of said bridge on the centrifuge cup.

5. The bridge as set forth in claim 3 wherein said cross member includes a curved surface for placement of a portion of the blood collection bag thereupon.

6. The bridge as set forth in claim 5 wherein said pins extend from said curved surface.

7. The bridge as set forth in claim 1 wherein said cross member includes means for frictionally engaging the blood collection bag upon centrifugation of the blood collection bag to assist in retaining the blood collection bag suspended from said cross member during centrifugation.

8. The bridge as set forth in claim 7 wherein each guide member of said pair of guide members includes means for seating said pair of guide members upon the edge of the centrifuge cup.

9. A bridge for serially suspending a blood collection bag within a centrifuge cup having an edge circular in planform at its open upper end and from an expressor, which expressor includes a plate, said bridge comprising in combination:
   (a) a pair of guide member means for engaging and receiving support from the upper edge of the centrifuge cup;
   (b) a cross member extending between said guide member means;
   (c) means for suspending the blood collection bag from said cross member; and
   (d) means for supporting said bridge upon the expressor to place the blood collection bag into operative relationship with the expressor said supporting means including a part of said cross member.

10. The bridge as set forth in claim 9 wherein said supporting means includes a stud extending from said cross member and said pair of guide member means.

11. The bridge as set forth in claim 10 wherein said stud and said pair of guide member means collectively define a three point support for mounting said bridge upon the expressor.

12. The bridge as set forth in claim 9 wherein said supporting means is formed as a part of said pair of guide member means.

13. The bridge as set forth in claim 12 wherein said supporting means comprises a slot disposed in each guide member of said pair of guide member means for receiving a part of the expressor and for mounting said bridge upon the expressor.

14. The bridge as set forth in claim 9 wherein each guide member means of said pair of guide member means includes means for seating said pair of guide member means upon the edge of the centrifuge cup.

15. The bridge as set forth in claim 14 wherein each of said seating means defines an arc commensurate with a segment of the edge of the centrifuge cup.

16. The bridge as set forth in claim 9 wherein said cross member includes means for frictionally engaging the blood collection bag upon centrifugation of the blood collection bag to assist in retaining the blood collection bag suspended from said cross member.

17. The bridge as set forth in claim 16 wherein each guide member means of said pair of guide member means includes means for seating said pair of guide member means upon the edge of the centrifuge cup.

18. A bridge for suspending a blood collection bag within a centrifuge cup having an edge circular in planform at its open upper end, said bridge comprising in combination:
   (a) guide member means for engaging and receiving support from the upper end of the centrifuge cup said guide member means including means for seating said guide member upon the edge of the centrifuge cup; and
   (b) means for suspending the blood collection bag from said guide member means.

19. The bridge as set forth in claim 18 wherein said seating means defines an arc commensurate with a segment of the edge of the centrifuge cup.

20. The bridge as set forth in claim 18 wherein said suspending means comprises a bracket extending from said guide member means.

21. The bridge as set forth in claim 20 wherein said bracket includes pin means for penetrably engaging the blood collection bag.

22. The bridge as set forth in claim 18 wherein said guide member means includes means for mounting said guide member means and blood collection bag suspended therefrom operatively associated with an expressor for expressing the contents of the blood collection bag.

23. The bridge as set forth in claim 22 wherein said mounting means includes at least one slot.

24. The bridge as set forth in claim 22 wherein said mounting means includes a pair of slots.

25. The bridge as set forth in claim 22 wherein said guide member means includes means for seating said guide member means upon the edge of the centrifuge cup.

26. The bridge as set forth in claim 25 wherein said suspending means comprises a bracket extending from said guide member means.

27. The bridge as set forth in claim 18 wherein said guide member means comprises a pair of opposed guide members.

28. The bridge as set forth in claim 27 wherein said suspending means comprises a cross member interconnecting said pair of guide members.

29. The bridge as set forth in claim 28 wherein said cross member comprises a pair of telescoping rods.

30. The bridge as set forth in claim 29 wherein said pair of telescoping rods includes means for penetrably engaging the blood collection bag to suspend the blood collection bag therefrom.

31. The bridge as set forth in claim 30 including means for positioning the blood collection bag with respect to said pair of telescoping rods.

32. The bridge as set forth in claim 29 including means for mounting said pair of guide members and blood collection bag suspended therefrom operatively associated with an expressor for expressing the contents of the blood collection bag.

33. The bridge as set forth in claim 32 wherein said mounting means includes at least one slot.

34. The bridge as set forth in claim 32 wherein said mounting means includes a pair of slots.

35. The bridge as set forth in claim 29 wherein said pair of guide members includes means for seating said pair of guide members upon the edge of the centrifuge cup.

36. A method for suspending a blood collection bag in a centrifuge cup having an edge circular in planform at its open upper end, said method comprising the steps of:
   (a) locating a bridge at the upper end of a centrifuge cup, including the step of seating the bridge upon the edge; and
   (b) suspending the blood collection bag from the bridge into the centrifuge cup.

37. The method as set forth in claim 36 wherein said step of suspending includes the step of penetrably engaging an upper end of the blood collection bag.

38. The method as set forth in claim 36 including the step of mounting the bridge upon an expressor in an operative relationship to effect expression of stratified contents of the blood collection bag subsequent to exercise of said step of locating and suspending.

39. The method as set forth in claim 38 wherein said step of mounting includes the step of positioning a part of the expressor into a part of the bridge.

40. The method as set forth in claim 36 including the step of increasing the force to suspend the blood collection bag from the bridge as a function of the centrifuged force exerted during centrifugation of the blood collection bag.

41. A method for segregating the major components of whole blood contained in a blood collection bag, said method comprising the steps of:
   (a) suspending the blood collection bag from the upper edge of a centrifuge cup prior to centrifugation of the whole blood;
   (b) mounting the blood collection bag upon an expressor in an operative relationship therewith to accommodate expressing the stratified components in the blood collection bag after the whole blood has been centrifuged; and
   (c) supporting the blood collection bag in a depending relationship from a bridge during exercise of said steps of suspending and mounting.

42. The method as set forth in claim 41 including the step of increasing the force to suspend the blood collection bag from the bridge as a function of the centrifuged force exerted during centrifugation of the blood collection bag.

* * * * *

UNITED STATES PATENT AND TRADEMARK OFFICE
CERTIFICATE OF CORRECTION

PATENT NO. : 4,909,949

DATED : March 20, 1990

INVENTOR(S) : Harmony, et al

Page 1 of 2

It is certified that error appears in the above-identified patent and that said Letters Patent is hereby corrected as shown below:

The sheet of drawings, consisting of Figs. 6,7,8 and 9 should be added as shown on the attached page.

Signed and Sealed this

Thirty-first Day of December, 1991

Attest:

HARRY F. MANBECK, JR.

*Attesting Officer*  *Commissioner of Patents and Trademarks*

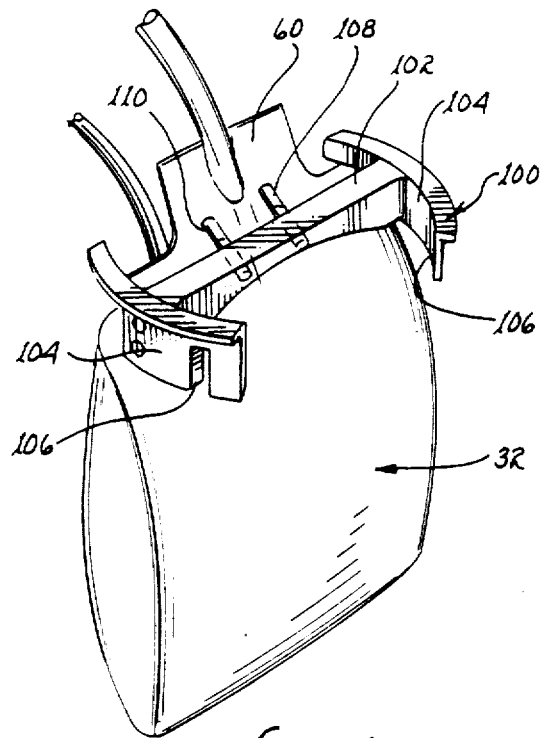
fig. 6
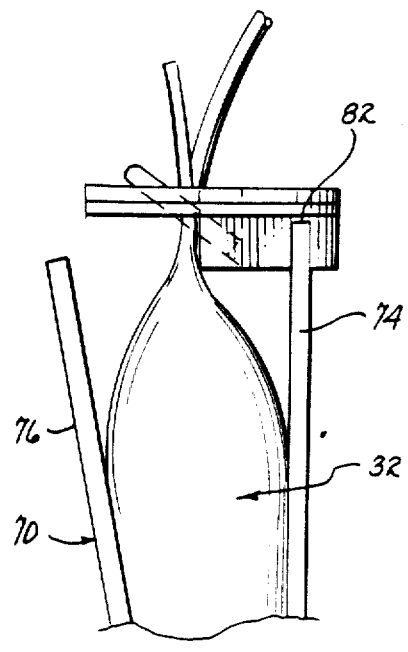
fig. 7
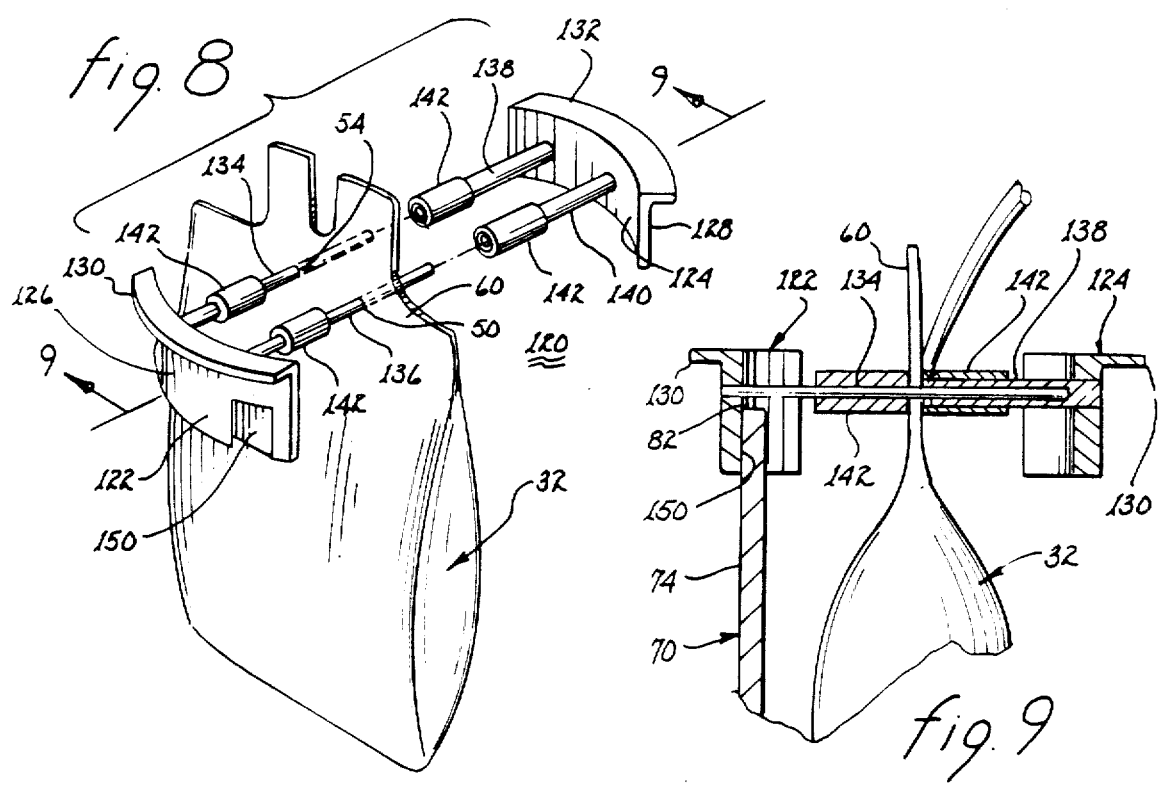
fig. 8
fig. 9